United States Patent [19]

Georgevich

[11] 4,291,697

[45] Sep. 29, 1981

[54] CLEANING AND APPLICATION DEVICE FOR MEDICAL PURPOSES

[76] Inventor: Stephen Georgevich, 4741 Royce Rd., Irvine, Calif. 92715

[21] Appl. No.: 141,416

[22] Filed: Apr. 18, 1980

[51] Int. Cl.³ ............................................ A61M 35/00
[52] U.S. Cl. .................................... 128/269; 401/132
[58] Field of Search ............. 128/260, 270, 269, 296; 401/132, 200; 15/244 R, 244 C, 245

[56] References Cited

U.S. PATENT DOCUMENTS

| | | | |
|---|---|---|---|
| 3,060,486 | 10/1962 | Lewis | 401/132 |
| 3,556,667 | 1/1971 | Kaufman | 401/132 |
| 3,614,245 | 10/1971 | Schwartzman | 128/269 |
| 3,768,916 | 10/1973 | Avery | 401/132 |
| 3,981,304 | 9/1976 | Szpur | 128/269 |
| 4,027,985 | 6/1977 | Loesser | 128/269 |
| 4,148,318 | 4/1979 | Meyer | 128/269 |

FOREIGN PATENT DOCUMENTS

1190521 4/1959 France .................................. 401/200

*Primary Examiner*—C. Fred Rosenbaum
*Attorney, Agent, or Firm*—Willie Krawitz

[57] ABSTRACT

A cleaning device for medical purposes is provided, comprising a sealable sponge portion which encapsulates a pressure rupturable pouch containing liquid of a cleaning, antiseptic or similar nature, the pouch being sealed within the sponge. The sponge and pouch are usually sterilized following manufacture and packaging.

Just prior to use, pressure is applied to the exterior of the sponge causing the pouch to rupture. This forces the liquid ingredients to spread outwardly from the sponge interior to the surface of the sponge. A fairly uniform supply of liquid on the sponge surface is thereby made available for use.

A non-woven absorbent material may be sealed inside the sponge to absorb some of the liquid when it is released from the ruptured pouch. The absorbent material also functions to distribute the liquid along the sponge and provide a more uniform supply of liquid to the sponge surface.

13 Claims, 7 Drawing Figures

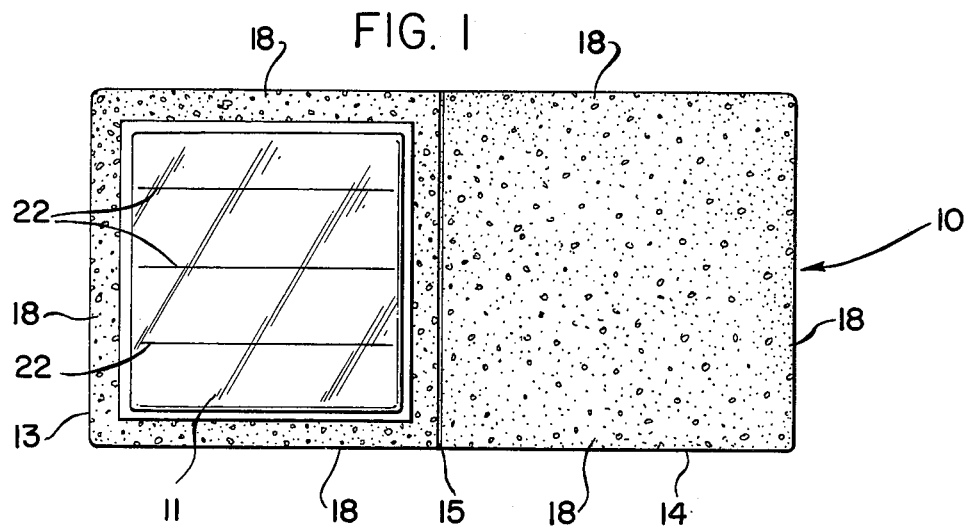
FIG. 1
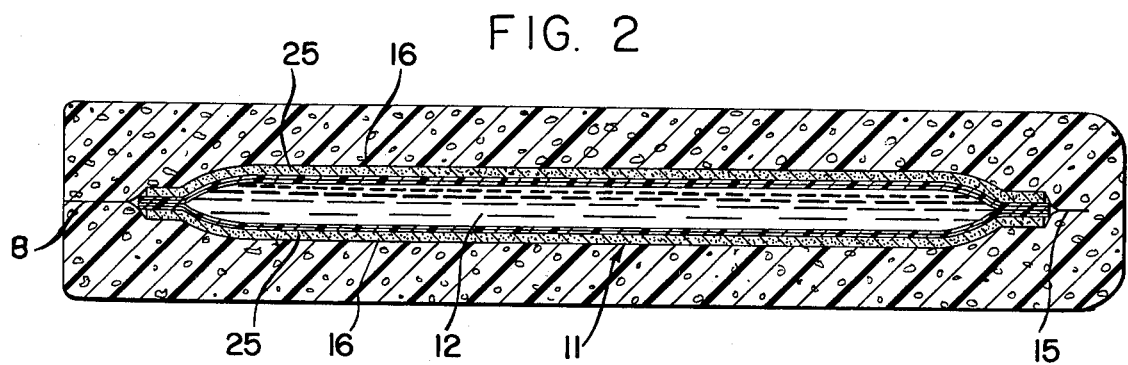
FIG. 2
FIG. 3
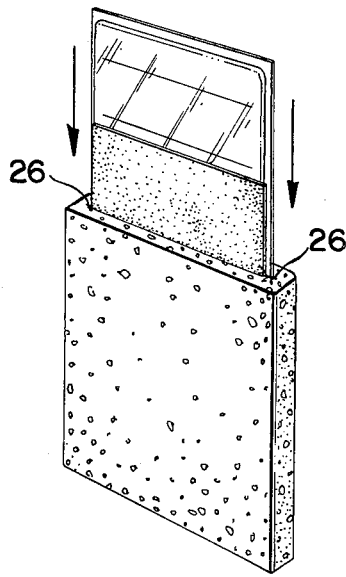
FIG. 4
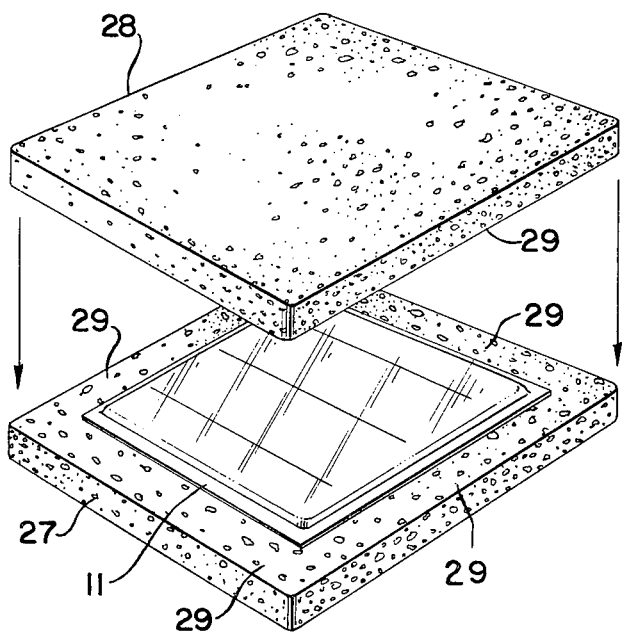

CLEANING AND APPLICATION DEVICE FOR MEDICAL PURPOSES

BACKGROUND OF THE INVENTION

This invention relates to a cleaning and applicator device, and more specifically, to a device providing antiseptic and cleaning action for medical purposes such as pre and post surgery, in sterile procedures, and the like.

Various types of cleaning devices, particularly of the sponge type, have been employed for pre-surgical purposes, and typical patents disclosing this technology are found in U.S. Pat. Nos. 3,482,920; 3,876,314; 3,891,331; 4,027,985; 4,148,318; U.S. Pat. No. De. 245,390 (Design); and, French Pat. No. 1,161,656.

Some of the surgical cleaning devices disclosed in these patents are expensive and difficult to produce with conventional manufacturing equipment. In other cases, the devices do not provide an ample supply of liquid over a sufficiently wide area of cleaning surface. In other instances, it is difficult to sterilize the device readily. In still other instances, the means for initiating the flow of liquid to the device and for maintaining an even distribution of liquid to the device while in use is both awkward or impractical.

Consequently, a new and improved antiseptic and cleaning device for medical purposes is desired which is easy and inexpensive to manufacture, package and sterilize, and is also convenient to use. Preferably, a reasonably uniform mounting of cleaning ingredients should be distributed along the surface of the device to facilitate a cleaning or antiseptic procedure.

THE INVENTION

According to the invention, a cleaning device for medical purposes is provided, comprising: a sponge portion; and a pouch sealed within the sponge and containing liquid cleaning or antiseptic ingredients, and the like for medical purposes. The pouch is provided with weakening lines or areas thereon for rupturing upon the application of pressure, whereby when sufficient pressure is applied to the sponge, the pouch will rupture and liquid will be formed to the sponge surface and be made available for medical purposes such as application to a patient, for cleaning areas in the vicinity of the patient, for cleaning certain types of medical equipment, etc.

If desired, a thin sheet of absorbent material may be disposed within the sponge in the vicinity of the pouch to absorb a portion of the liquid ingredients when the pouch is ruptured. These liquid ingredients are transmitted along the absorbent material and through the interior of the sponge to the surface along with the remaining liquid. The overall effect is to produce a fairly even distribution of liquid over the sponge surface. Since the liquid tends to spread over the entire sponge, this enables the user to employ an effectively larger sponge area when applying scrubbing or antiseptic liquid to a patient; hence, this produces quick and effective results for pre and post surgery use. During application, and when scrubbing, continued pressure on the sponge causes additional liquid to be forced to the sponge surface and provides a continuing supply for application to the patient, and the like.

BRIEF DESCRIPTION OF THE DRAWINGS

FIG. 1 is a plan view of one embodiment of the invention showing the sponge and pouch prior to sealing the pouch within the sponge;

FIG. 2 is a view in sectional side elevation showing an assembled sponge, sealed-in-pouch containing liquid, and surrounded by a sheet of absorbent material;

FIGS. 3 and 4 are perspective views showing different embodiments of the sponge and pouch assembly prior to sealing;

DESCRIPTION OF THE PREFERRED EMBODIMENT

Figure 5:
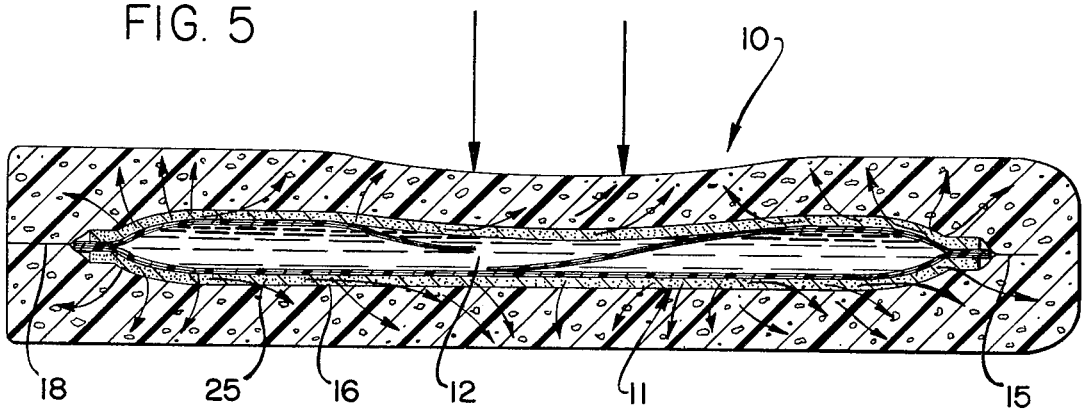
FIG. 5 is a view in sectional side elevation showing the effect of rupturing the pouch by applied pressure on the sponge.

The cleaning device 10 of this invention, as applied to say pre-surgery, is shown in FIG. 1 together with a pouch 11 containing a solution 12 of cleaning ingredients or antiseptic, etc., the assembly of sponge and pouch being shown prior to sealing the pouch within the sponge.

The sponge 10 is constructed of a polymeric foam such as a polyurethane or other suitable foam material which are available in a variety of densities and porosities. This enables a coarse type of sponge to be used for patient scrubbing, and a finer type of sponge for applying antiseptic. In any event, the foam structure should be sufficiently small to absorb the liquid and prevent it from running off the surface. In the embodiment shown in FIG. 1, the sponge 10 is shown in an open position, prior to assembly, and comprises segments 13, 14 and a fold notch 15; this facilitates folding the segments together at the outset of pouch encapsulation. As the segments are folded around the pouch, pressure on the pouch will cause it to form a cavity 16 within the sponge as shown in FIG. 2. However, if desired, each segment 13 and 14 may be configured to define a partial cavity shape which seats the encapsulated pouch; of course, this will increase the cost of the device. After fold-over of the segments 13 and 14, the edges 18 are then sealed by heating, adhesives, etc., to produce an encapsulated product. If a handle is to be incorporated into the sponge, it is inserted at this stage of the process.

The pouch may be constructed of a thin wall film comprising a laminate having an outer layer of polyester (mylar) and an inner layer of polyethylene; a typical laminate thickness may vary from about 3-8 mils. Another suitable thin wall pouch material includes a sealed laminate of thin foil aluminum and polyethylene.

Typically, the pouch bears one or more weakening lines 22 embossed on the surface and adapted to rupture when sufficient pressure is applied to the pouch through the sponge; rupture of the pouch will release the antiseptic or cleaning solution 12 into the sponge 10 as shown in FIG. 5. Obviously, the pouch structure, when encapsulated in the polyurethane sponge, should be sufficiently resistant to impact and shock so that it will not rupture during routine handling and transit activities.

Liquids which may be used as the solution 12 include polyvinylpyrrolidone-iodine (PVP-iodine), iodophors, antiseptic soaps such as green soap, PVP scrub solution, PHISOHEX, fungicides, etc.

A non-woven material such as paper, rayon or cotton may be used as the absorbent sheet 25 for transmitting liquid from the pouch and along the sheet by capillary action when the pouch is ruptured. One suitable material is sold under the trade name of "MASSLIN" by Johnson & Johnson, (Chicopee Division). The absorbent sheet 25 may be applied along the sponge prior to sealing as in FIG. 2. Alternatively, the sheet may be simply compressed and inserted into the open end of the sponge prior to sealing. Use of the non-woven absorbent is desirable when associated with a coarse, highly porous sponge, and it is desired to prevent a too rapid 'strike through' of the liquid when the pouch is ruptured.

FIGS. 3 and 4 illustrate alternative embodiments for encapsulation of the sponge. In FIG. 3, the sponge is slit at one end to provide an opening 26, and the pouch is inserted through the opening into the sponge which is then edge-sealed. In FIG. 4, the pouch is supported on an individual sponge segment 27, and a corresponding upper segment 28 is superposed over the segment 27 and then moved downwardly into registry with segment 27; the two segments 27, 28 are then heat sealed along their edges 29.

Figure 6:
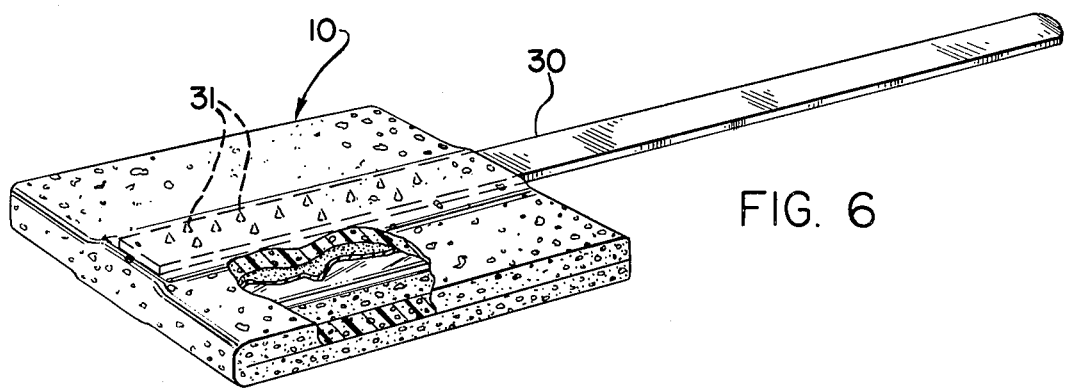
FIG. 6 is a perspective view illustrating a sponge, encapsulated pouch and absorbent material together with a plastic handle; and, FIG. 7 is a view in sectional side elevation showing a sponge encapsulating a pouch filled with water for combination with dried cleaning or sterilizing material that has been impregnated into the sponge.

In FIG. 6, a plastic handle 30 is shown glued to the sponge to facilitate scrubbing and also to avoid hand contact with the sponge. The plastic handle may be manufactured of polypropylene for ease of sterilization, and may be T-shaped in cross section to improve rigidity. If desired, a plurality of puncture projections 31 are provided at the end of the handle to pierce the pouch and release liquid when pressure is applied.

Figure 7:
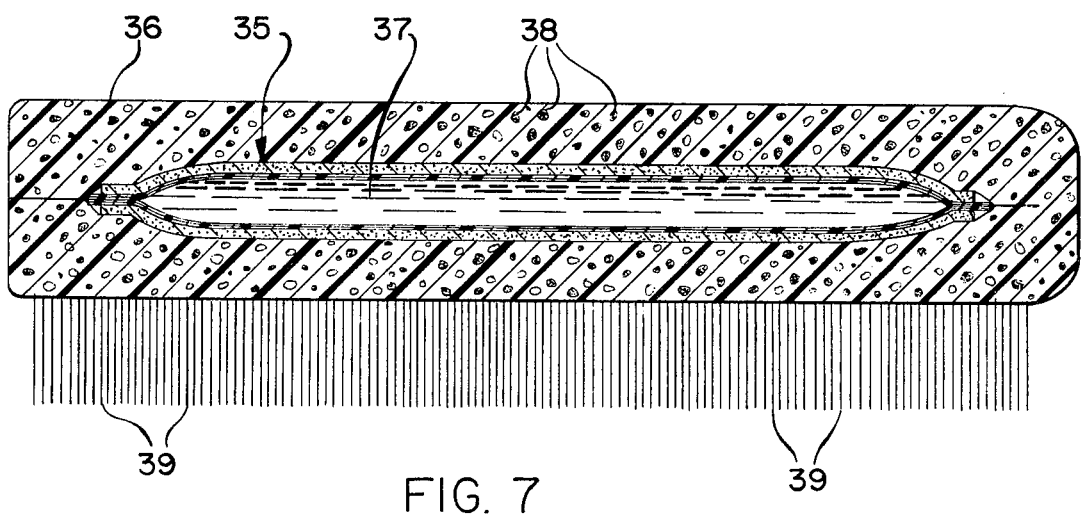

An alternative embodiment is shown in FIG. 7, and comprises a pouch 35 disposed in a sponge 36, the pouch containing water 37 which is preferably sterilized. An antiseptic or soap 38 is impregnated in the sponge so that rupture of the pouch will release water to combine with the soap or antiseptic for transmission to the sponge surface. This embodiment is particularly useful because it enables a surgeon to clean his hands with totally sterile materials rather than using ordinary tap water with an antiseptic soap. A plurality of bristles 39 may be provided on the sponge to assist in the cleaning procedure.

Usually, the sponge and encapsulated pouch are sterilized in an atmosphere containing ethylene oxide; sterilization conditions vary from about 145° C.–165° C. for about 4–12 hours, depending on the ethylene oxide concentration. Other sterilization procedures may be employed, where appropriate, such as with a cobalt 60 source.

As indicated, a preferred laminate orientation employs mylar on the outside of the pouch to resist impregnation of the laminate by the ethylene oxide and thereby reduces the possibility of reaction with the PVP-iodine solution. The inner layer being polyethylene, is readily heat sealable by rf heating, hot adhesive bonding, etc. Thus sterilization of the sponge and exterior of the pouch which contains the PVP-iodine solution is accomplished by exposure in an ethylene oxide medium, while the interior of the pouch is sterilized by the antiseptic solution itself.

The cleaning device of this invention is inexpensive and easy to manufacture and sterilize, and is extremely simple to use. For example, if a sponge containing an encapsulated pouch is sterilized in a peel-open package, a 'non-sterile' user will be enabled to rupture the pouch by applying pressure on the outside of the package. The package is then peeled open by the 'non-sterile' user and allows a 'sterile user' to withdraw the sterile device without contamination. Furthermore its construction permits the cleaning solution to be applied to a patient from a broad area of sponge; this in turn permits a uniform and effective scrubbing action in a reasonable length of time.

The cleaning device can be readily stored, shipped and handled in a unitary package without significant problems arising from a potential rupture of the liquid containing pouch. If a leak does occur, it will be immediately self evident, and the particular sponge can be discarded.

Finally, the pouch, sponge and absorbant sheet arrangement enables the sponge to be configured in a wedge shape, pie shape, tubular configuration, etc., for cleaning specific areas of a patient's body while still maintaining an adequate supply of soap or antiseptic to the sponge. A blister type of package may be utilized as the pouch to contain the cleaning, antiseptic liquid, and the like without departing from the spirit of this invention.

It will be appreciated that a wide variety of uses may be afforded this invention within the spirit thereof. For example, the cleaning device may be utilized for preoperative procedures, post operative wound care, in child delivery, and for cleaning cuts, burns and abrasions, prior to treatment, etc. It also may be used to clean some types of surgical instruments which are not readily sterilizable in a steam or liquid medium and to clean patient's rooms to reduce the possibility of infections of the staphlococcus py. var. aureus types, etc.

Finally, it will be appreciated that the term "sponge" referring to the absorbent, also includes non-woven materials which are not necessarily of polymeric origin, such as rayon.

I claim:

1. A sterilizable, cleaning device for medical purposes, comprising:
    (a) a sponge element;
    (b) a pouch disposed within the sponge, the pouch containing cleaning or antiseptic liquids, the sponge being edge sealed along at least one side to completely encapsulate the pouch therein, the pouch comprising:
        i. a rupturable film selected from the class consisting of plastic, plastic laminate, and a laminate of aluminum and plastic,
        ii. the pouch bearing one or more weakening lines thereon adapted to be ruptured under pressure; and
    (c) a handle defining two ends and a medial area, a portion of the medial area being sealed within the sponge, and adjacent the pouch, whereby pressure on the sponge and handle ruptures the weakening lines, thereby releasing the liquid from the pouch, a portion of liquid being absorbed by the sponge, the remaining liquid passing outwardly through the sponge and along its surface, and pressure on the sponge while scrubbing forces absorbed liquid to the sponge surface to provide a continuing supply of liquid on the sponge surface for application thereof.

2. The cleaning device of claim 1, comprising a laminated pouch having an outer layer of polyester film and an inner layer of polyethylene film.

3. The cleaning device of claim 1, comprising: a non-woven material disposed within the sponge for absorbing some of the liquid and distributing the liquid throughout the sponge.

4. The cleaning device of claim 1, in which the liquid in the pouch is water and the sponge is impregnated with a dried soap, antiseptic material and the like.

5. The cleaning device of claim 1, in which a plurality of puncture points are disposed on the said medial area portion, whereby pressure on the sponge and handle punctures the pouch and ruptures the weakening lines.

6. The cleaning device of claim 5, in which the handle is flat shaped and the puncture points are disposed on the flat area adjacent the pouch.

7. The cleaning device of claim 5, in which the sponge is sterilized by ethylene oxide or radiation, and the liquid in the pouch contains an iodine compound.

8. A method for supplying cleaning or antiseptic liquids and the like for medical purposes to a cleaning device, comprising:
   (a) a sponge element;
   (b) a pouch disposed within the sponge, the pouch containing cleaning or antiseptic liquids, the sponge being edge sealed along at least one side to completely encapsulate the pouch therein, the pouch comprising:
      i. a rupturable film selected from the class consisting of plastic, plastic laminate, and a laminate of aluminum and plastic,
      ii. the pouch bearing one or more weakening lines thereon adapted to be ruptured under pressure; and
   (c) a handle defining two ends and a medial area, a portion of the medial area being sealed within the sponge, and adjacent the pouch; the steps comprising:
      i. applying pressure on the sponge and handle thereby rupturing the weakening lines, and releasing liquid from the pouch;
      ii. absorbing a portion of the released liquid by the sponge;
      iii. passing the remaining liquid outwardly through the sponge and along its surface; and,
      iv. applying pressure on the handle or sponge to provide a continuing supply of liquid to the sponge surface for application thereof.

9. The method of claim 8, in which a non-woven sheet is disposed within the sponge to absorb some of the liquid and distribute the absorbed liquid in a uniform manner to the sponge surface.

10. The method of claim 8, in which the liquid in the pouch is sterilized water and the sponge is impregnated with a dried soap or antiseptic material, and the like.

11. The method of claim 8, in which the device is sterilized in a package, the pressure is applied to rupture the pouch, and the package is opened for withdrawal of the device in a sterile condition.

12. The method of claim 8, in which a plurality of puncture points are integral with the said medial area portion of the handle, whereby pressure on the sponge and handle punctures the pouch and ruptures the weakening lines.

13. The method of claim 12, in which the handle is flat shaped and the puncture points are integral with the flat area adjacent the pouch.

* * * * *